US007687628B2

(12) United States Patent
Gutman et al.

(10) Patent No.: US 7,687,628 B2
(45) Date of Patent: Mar. 30, 2010

(54) METHOD OF PREPARING 4-AMINO-1H-IMIDAZO(4,5-C)QUINOLINES AND ACID ADDITION SALTS THEREOF

(75) Inventors: Daniella Gutman, Rishon Lezion (IL); Wael Baidossi, Hamesholash (IL); Shimon Chernyak, Yokneam Ilit (IL)

(73) Assignee: Taro Pharmaceuticals U.S.A., Inc., Hawthorne, NY (US)

( * ) Notice: Subject to any disclaimer, the term of this patent is extended or adjusted under 35 U.S.C. 154(b) by 948 days.

(21) Appl. No.: 10/956,465

(22) Filed: Sep. 30, 2004

(65) Prior Publication Data
US 2005/0085500 A1 Apr. 21, 2005

Related U.S. Application Data

(60) Provisional application No. 60/507,557, filed on Oct. 1, 2003.

(51) Int. Cl.
C07D 491/06 (2006.01)
A61K 31/44 (2006.01)
(52) U.S. Cl. .................................. 546/82; 514/292
(58) Field of Classification Search ................ 546/82; 514/292
See application file for complete search history.

(56) References Cited

U.S. PATENT DOCUMENTS

| 4,689,338 | A | 8/1987 | Gerster |
| 4,698,348 | A | 10/1987 | Gerster |
| 4,929,624 | A | 5/1990 | Gerster et al. |
| 5,037,986 | A | 8/1991 | Gerster |
| 5,175,296 | A | 12/1992 | Gerster |
| 5,346,905 | A | 9/1994 | Gerster |
| 5,352,784 | A | 10/1994 | Nikolaides et al. |
| 5,367,076 | A | 11/1994 | Gerster |
| 5,389,640 | A | 2/1995 | Gerster et al. |
| 5,395,937 | A | 3/1995 | Nikolaides et al. |
| 5,494,916 | A | 2/1996 | Lindstrom et al. |
| 5,578,727 | A | 11/1996 | Andre et al. |
| 5,741,908 | A | 4/1998 | Gerster et al. |
| 6,069,149 | A * | 5/2000 | Nanba et al. ............. 514/293 |
| 6,194,425 | B1 | 2/2001 | Gerster et al. |
| 6,255,502 | B1 * | 7/2001 | Penkler et al. ............. 552/549 |
| 6,376,669 | B1 | 4/2002 | Rice et al. |
| 6,583,317 | B1 * | 6/2003 | Moens ......................... 562/567 |
| 6,608,201 | B2 | 8/2003 | Gerster et al. |
| 6,624,305 | B2 | 9/2003 | Gerster et al. |
| 2004/0138459 | A1 | 7/2004 | Merli et al. |

FOREIGN PATENT DOCUMENTS

| EP | 145340 | 1/1990 |
| EP | 310950 | 1/1993 |
| WO | WO98/30562 | * 7/1998 |
| WO | WO 1999/029693 | 6/1999 |

| WO | WO 2004/009593 A1 | 1/2004 |

OTHER PUBLICATIONS

Tam James et al 1986, m Mechanism for the removal of benzyl proecting group . . . .*
Wikepedia definition of hydrogelysis 2008.*
Shen et al., "Study on the synthesis of imiquimod," Chem. Res. & Appln., 2001, 13, 249-252 (original Chinese and certified English translation).
Aggarwal et al., "Highly diastereoselective nitrone cycloaddition onto a chiral ketene equivalent: Asymmetric synthesis of cispentacin," Org. Lett., 2002, 4, 1227-1229.
S.L. Seager & M.R. Slabaugh, "Chemistry for Today: General, Organic, and Biochemistry," Brooks/Cole (2000) pp. 285-286.
"Hydrolysis," Wikipedia, http://en.wikipedia.org/w/index.php?title=Hydrolysis&printable=yes, accessed Dec. 15, 2008 (5 pages).
R.T. Morrison & R.N. Boyd, "Organic Chemistry," $3^{rd}$ ed., Allyn and Bacon (1976) pp. 680-684.
G.V. Smith & F. Notheisz, "Heterogeneous Catalysis in Organic Chemistry," Academic Press (1999) pp. 119, 160-180, 202-218.
B.L. Hutchings et al., "A Chemical Method for the Determination of Pteroylglutamic Add and Related Compounds," J. Biological Chem., v. 168 (1947) pp. 705-710.
H.T. Clarke et al., "The Action of Formaldehyde on Amines and Amino Acids," J. Am. Chem. Soc., v. 55 (Nov. 1933) pp. 4571-4587.
V.I. Maksimov & N.D. Zelinskii, "Fragmentation of activated n,n-dibenzyl-3-phenylalanine derivatives," Russian Chem. Bulletin, v. 11, n. 1 (Jan. 1962) pp. 99-105 (English-language summary, http://www.springerlink.com/content/m54528x4607154x1/, accessed Nov. 29, 2006 (3 pages)).
M.G. Loudon, "Organic Chemistry," Addison-Wesley (1984) p. 1059.
"Amine," Wikipedia, http://en.wikipedia.orq/w/index.php?title=Amine&printable=yes, accessed Feb. 1, 2008 (8 pages).
International Search Report (Apr. 28, 2005) for PCT/US2004/032243.
International Preliminary Report on Patentability (Apr. 3, 2006) and Written Opinion (Apr. 28, 2005) for PCT/US2004/032243.

* cited by examiner

*Primary Examiner*—Rita J Desai
(74) *Attorney, Agent, or Firm*—Venable LLP; Lars H. Genieser; Zayd Alathari

(57) ABSTRACT

The present invention provides a method of preparing a 4-(arylmethyl)amino-1H-imidazo(4,5-c)quinoline of formula (4) by reacting an arylmethylamine of formula (3) with a 4-chloro-1H-imidazo(4,5-c)quinoline of formula (2). The present invention further provides a method of preparing an acid addition salt of formula (5) comprising the step of hydrolyzing a 4-(arylmethyl)amino-1H-imidazo(4,5-c)quinoline of formula (4) with a strong acid, HX. The present invention further provides a method of preparing a 4-amino-1H-imidazo(4,5-c)quinoline of formula (1) comprising the step of treating an acid addition salt of formula (5) with a base.

20 Claims, No Drawings

METHOD OF PREPARING 4-AMINO-1H-IMIDAZO(4,5-C)QUINOLINES AND ACID ADDITION SALTS THEREOF

CROSS REFERENCE TO RELATED APPLICATION

This application claims the benefit under 35 U.S.C. § 119 (e) of U.S. Provisional Application No. 60/507,557, filed Oct. 1, 2003, the disclosure of which is incorporated by reference in its entirety herein.

BACKGROUND OF THE INVENTION

1. Technical Field

This invention provides a method of preparing drugs comprising tricyclic ring structures that possess 3 nitrogen atoms. More specifically, the invention provides a method of preparing 4-amino-1H-imidazo(4,5-c)quinolines and acid addition salts thereof.

2. Background Art 4-amino-1-isobutyl-1H-imidazo(4,5-c)quinoline (imiquimod; compound of formula (1), wherein $R^1$=isobutyl, $R^2$=H) is an immune-response modifier that induces various cytokines, including interferon-α. It is marketed as a 5% cream under the tradename ALDARA® (3M Pharmaceuticals, St. Paul, Minn.), and has been widely used to treat genital warts in humans.

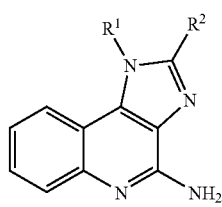

(1)

Two procedures for preparing a compound of formula (1) from the corresponding 4-chloro analog of formula (2) have been reported. The first procedure is a one-step ammonolysis procedure (Scheme 1).

Scheme 1

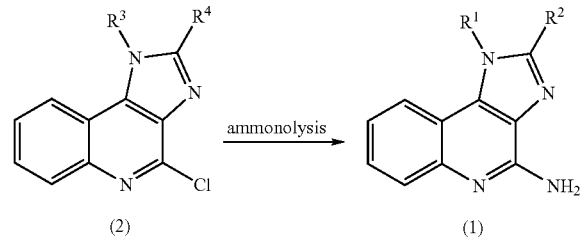

U.S. Pat. No. 4,689,338 ('338 patent) and Shen et al., Chem. Res. & Appln., 2001, 13, 249-252 (the Shen article), specifically disclose Scheme 1 procedures. The '338 patent discloses the reaction of the compound of formula (2) ($R^3$=methyl, isobutyl, 2,3-dihydroxypropyl, phenyl, 4-methoxyphenyl, or 4-fluorophenyl; $R^4$=hydrogen or methyl) with ammonia or ammonium hydroxide in a sealed vessel for 16-18 hours at 150° C.-155° C. The '338 patent does not disclose the obtained yield. The Shen article discloses the reaction of the compound of formula (2) ($R^3$=isobutyl; $R^4$=hydrogen) with aqueous ammonia in methoxy ethanol solvent in a sealed vessel for 4 hours at 100° C. The obtained yield of the compound of formula (1) ($R^1$=isobutyl, $R^2$=H) is reported to be 61%.

One disadvantage of the ammonolysis procedure (Scheme 1) is that the ammonolysis reaction must be conducted at elevated temperature in a sealed reaction vessel. This poses an undesirable safety risk.

The second procedure is a two-step procedure (Scheme 2). In the first step of the second procedure, a 4-chloro compound of formula (2) is subjected to an addition/elimination reaction with benzylamine to provide a benzylamino intermediate. In the second step of the second procedure, the benzylamino intermediate is hydrogenolyzed to provide a compound of formula (1).

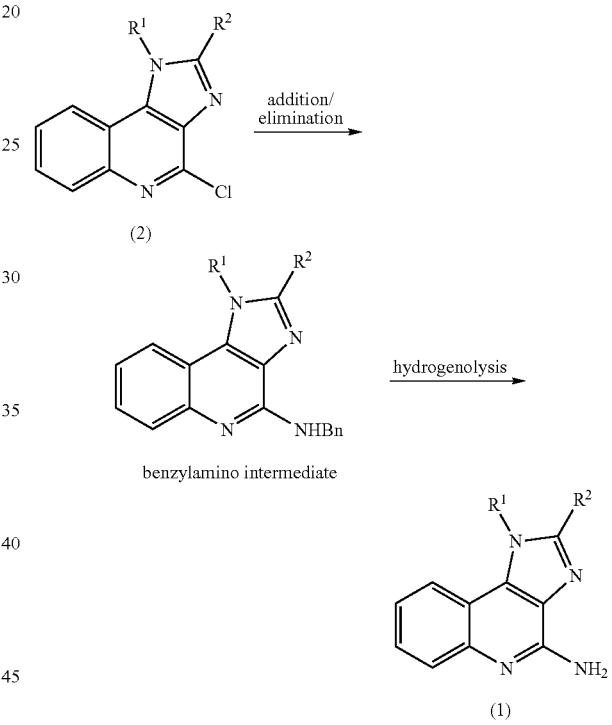

U.S. Pat. No. 6,069,149 ('149 patent) and the Shen article specifically disclose Scheme 2 procedures. The '149 patent discloses that the first step is performed by heating a compound of formula (2) ($R^3$=3-(tert-butoxycarbonylamino)propyl, 4-(tert-butoxycarbonylamino)butyl; $R^4$=hydrogen) in neat benzylamine for three hours. The benzylamino intermediate is isolated by distilling away excess benzylamine, and purified using silica gel column chromatography. The Shen article discloses that the first step is performed by heating a compound of formula (2) with benzylamine and potassium carbonate in methoxy ethanol solvent for eight hours. The benzylamino intermediate is isolated by distilling away the solvent.

The '149 patent discloses that the second step is performed by refluxing the benzylamino intermediate with Pd(OH)$_2$/C (Pearlman's catalyst) in a weak acid (i.e., formic acid) for 1-2 days. However, the yield of the compound of formula (1) ($R^1$=3-aminopropyl, 4-aminobutyl; $R^2$=H) is reported only to be 37-42%. The Shen article discloses an attempt to perform the second step by heating the benzylamino intermediate with hydrogen and Pd/C at 80° C. under acidic conditions. The Shen article states that the attempt failed.

One disadvantage of the first step in the second procedure (Scheme 2) is that the reaction solvent must be removed by distillation to isolate the benzylamino intermediate. In addition, purification using silica gel chromatography is required when the addition/elimination reaction is performed neat in benzylamine. Such distillation and chromatography procedures are costly and undesirable on an industrial scale. One disadvantage of the second step in the second procedure (Scheme 2) is that the hydrogenolysis reaction is proven to be difficult, and proceeds at a low yield even after a long reaction time. Presently, there are no suitable alternatives for the hydrogenolysis reaction.

There is a continuing need for an improved method of preparing 4-amino-1H-imidazo(4,5-c)quinolines.

SUMMARY OF THE INVENTION

The present invention provides a method of preparing an acid addition salt of

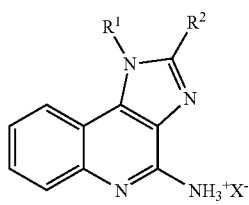

(5)

comprising the step of hydrolyzing a 4-(arylmethyl)amino-1H-imidazo(4,5-c)quinoline of formula (4) with a strong acid, HX,

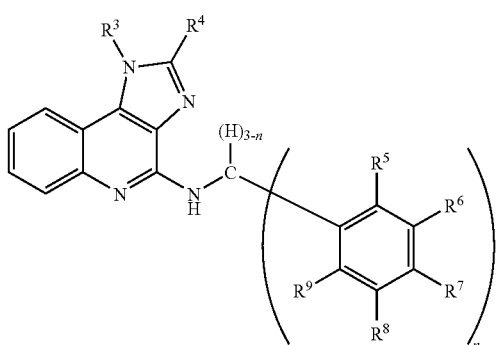

(4)

wherein
n is 1 or 2,
$R^1$, $R^2$, $R^3$ and $R^4$ are independently selected from the group consisting of hydrogen, $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl,
each of $R^5$, $R^6$, $R^7$, $R^8$, and $R^9$ for each of the n aryl rings is independently selected from the group consisting of hydrogen, $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, $C_6$-$C_{20}$ aryl, —$OR^{10}$, and —$NR^{11}R^{12}$, wherein $R^{10}$, $R^{11}$, and $R^{12}$ are independently selected from the group consisting of hydrogen and $C_1$-$C_{10}$ alkyl, and
$X^-$ is a conjugate base of a strong acid, thereby forming an acid addition salt of formula (5).

Preferably, the 4-(arylmethyl)amino-1H-imidazo(4,5-c)quinoline of formula (4) is prepared by reacting an arylmethylamine of formula (3)

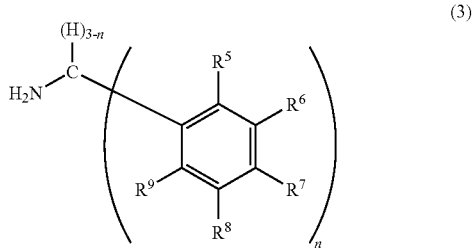

(3)

with a 4-chloro-1H-imidazo(4,5-c)quinoline of formula (2)

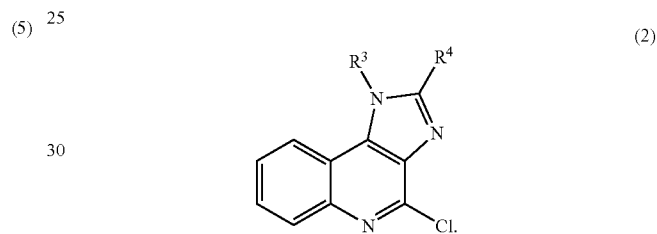

(2)

Preferably, the method further comprises the step of treating the acid addition salt of formula (5) with a base to provide a 4-amino-1H-imidazo(4,5-c)quinoline of formula (1)

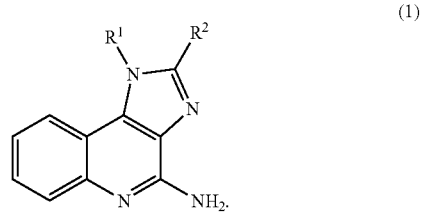

(1)

Preferably, the strong acid is selected from the group consisting of sulfuric acid, methanesulfonic acid, trifluoromethanesulfonic acid, and mixtures thereof.

Preferably, the base is selected from the group consisting of sodium hydroxide, potassium hydroxide, and mixtures thereof.

Preferably, $R^1$, $R^2$, $R^3$, and $R^4$ are independently selected from the group consisting of hydrogen, $C_1$-$C_{10}$ alkyl, and $C_6$-$C_{20}$ aryl, and each of $R^5$, $R^6$, $R^7$, $R^8$, and $R^9$ for each of the n aryl rings is independently selected from the group consisting of hydrogen, $C_1$-$C_{10}$ alkyl, $C_6$-$C_{20}$ aryl, —$OR^{10}$, and —$NR^{11}R^{12}$. More preferably, n is 1, $R^1$ and $R^3$ are independently $C_1$-$C_{10}$ alkyl, $R^2$ and $R^4$ are hydrogen, $R^5$, $R^6$, $R^7$, $R^8$, and $R^9$ are independently selected from the group consisting of hydrogen, $C_1$-$C_{10}$ alkyl, and —$O(C_1$-$C_{10}$ alkyl), and $X^-$ is selected from the group consisting of $HSO_4^-$, $CH_3SO_3^-$, and $CF_3SO_3^-$. More preferably, $R^1$ and $R^3$ are isobutyl. More preferably, $R^5$, $R^6$, $R^7$, $R^8$, and $R^9$ are hydrogen.

Preferably, the 4-amino-1H-imidazo(4,5-c)quinoline of formula (1) is 4-amino-1-isobutyl-1H-imidazo(4,5-c)quinoline (imiquimod).

Preferably, the hydrolyzing step is performed for a reaction time of less than about four hours. More preferably, the hydrolyzing step is performed for a reaction time of less than about two hours.

Preferably, the acid addition salt of formula (5) is obtained in a yield of at least about 70%. More preferably, the acid addition salt of formula (5) is obtained in a yield of at least about 80%.

Preferably, the arylmethylamine of formula (3) is selected from the group consisting of benzylamine, 2,4-dimethoxybenzylamine, diphenylmethylamine, and 1-(aminomethyl)naphthalene.

Preferably, the 4-(arylmethyl)amino-1H-imidazo(4,5-c)quinoline of formula (4) is prepared in a neat reaction.

Preferably, the 4-(arylmethyl)amino-1H-imidazo(4,5-c)quinoline of formula (4) is prepared at a temperature of about 100° C. to about 140° C.

DETAILED DESCRIPTION OF THE INVENTION

Definitions

"Hydrolyzing" refers to performing a hydrolysis reaction; "hydrolysis" refers to a chemical reaction that uses water (i.e., $H_2O$) to cleave a chemical bond; "hydrogenolyzing" refers to performing a hydrogenolysis reaction; "hydrogenolysis" refers to a chemical reaction that uses hydrogen (i.e., $H_2$) to cleave a chemical bond; "ammonolysis" refers to a chemical reaction that uses ammonia (i.e., $NH_3$) to cleave a chemical bond; "chemical bond" refers to the force that holds atoms together in molecules or crystals; "strong acid" refers to an acid having a $K_a$ (25° C.) of at least about 1; "acid addition salt" refers to a compound of formula $RH^+X^-$, wherein R is a molecule that contains at least one atom that can accept a proton from an acid, and $X^-$ is the conjugate base of an acid, HX; "neat reaction" refers to a reaction in which one or more of the reagents functions as a solvent; "solvent" refers to the most abundant component of a solution; "conjugate base" refers to a molecule that can be described as an acid that has lost one proton; "isolating" refers to separating a crude product from a reaction mixture; "crude product" refers to a reaction product that has been separated from the reaction, but not further purified; according the present invention, a "crude product" typically has a purity of at least about 80%; "purity" refers to the percentage by weight of the major component of a mixture; "purifying" refers to increasing the purity of a compound; "crystallizing" refers to inducing crystals to form in a solution; "heating" refers to adding thermal energy to a reaction mixture to raise the temperature of the reaction mixture above the ambient temperature of its surrounding environment (typically, the ambient temperature is about 22° C.).

The present invention provides an improved method of preparing 4-amino-1H-imidazo(4,5-c) quinolines. One unique feature of the present invention is that it involves employing a hydrolysis reaction. A strong acid may be used as a catalyst to drive the hydrolysis reaction. The hydrolysis reaction effectively provides an acid addition salt. A simple treatment of the acid addition salt with a base provides a 4-amino-1H-imidazo(4,5-c) quinoline. The present hydrolysis reaction provides a much better yield and a much shorter reaction time. Specifically, the present invention provides a method of preparing an acid addition salt of formula (5)

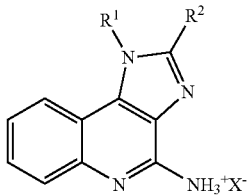

comprising the step of hydrolyzing a 4-(arylmethyl)amino-1H-imidazo(4,5-c)quinoline of formula (4) with a strong acid, HX,

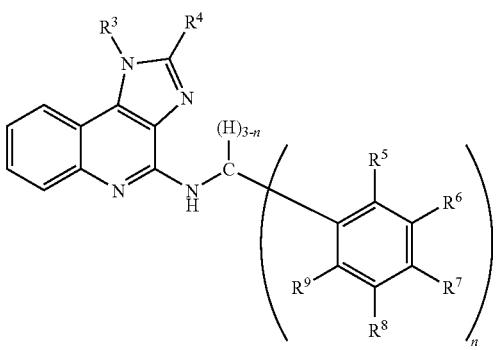

wherein
n is 1 or 2,
$R^1$, $R^2$, $R^3$ and $R^4$ are independently selected from the group consisting of hydrogen, $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl,
each of $R^5$, $R^6$, $R^7$, $R^8$, and $R^9$ for each of the n aryl rings is independently selected from the group consisting of hydrogen, $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, $C_6$-$C_{20}$ aryl, —$OR^{10}$, and —$NR^{11}R^{12}$,
wherein $R^{10}$, $R^{11}$, and $R^{12}$ are independently selected from the group consisting of hydrogen and $C_1$-$C_{10}$ alkyl, and
$X^-$ is a conjugate base of a strong acid, thereby forming an acid addition salt of formula (5).

Any suitable strong acid, HX, may be used in the hydrolysis reaction. A strong acid as used herein encompasses an acid having a $K_a$ (25° C.) of at least about 1. Preferably, the strong acid has a $K_a$ (25° C.) of at least about 10. More preferably, the strong acid has a $K_a$ (25° C.) of at least about 100. Tables of $K_a$ (25° C.) values are readily available (See, e.g., *CRC Handbook of Chemistry and Physics* (63d ed. 1982-83)). $K_a$ (25° C.) values also may be measured (See, e.g., Cookson, *Chem. Rev.* 1974, 74, 5-28).

Preferably, the strong acid includes, but is not limited to sulfuric acid, methanesulfonic acid, trifluoromethanesulfonic acid, and mixtures thereof. More preferably, the strong acid is sulfuric acid.

Preferably, the conjugate base of a strong acid (i.e., $X^-$) includes, but is not limited to $HSO_4^-$, $CH_3SO_3^-$, and $CF_3SO_3^-$. More preferably, $X^-$ is $HSO_4^-$.

n may be 1 or 2. Preferably, n is 1.

$R^1$, $R^2$, $R^3$, and $R^4$ may be identical or different. $R^1$, $R^2$, $R^3$, and $R^4$ may independently include, but are not limited to, hydrogen, $C_1$-$C_{10}$ alkyl, $C_3$-$C_{10}$ cycloalkyl, $C_2$-$C_{10}$ alkenyl, $C_5$-$C_{10}$ cycloalkenyl, $C_6$-$C_{20}$ aryl, and the like. Preferably, $R^1$, $R^2$, $R^3$, and $R^4$ may independently include, but are not limited to, hydrogen, $C_1$-$C_{10}$ alkyl, $C_2$-$C_{10}$ alkenyl, $C_6$-$C_{20}$ aryl, and the like. Preferably, $R^1$, $R^2$, $R^3$, and $R^4$ may independently include, but are not limited to, hydrogen, $C_1$-$C_{10}$ alkyl, $C_6$-$C_{20}$ aryl, and the like.

More preferably, $R^1$, $R^2$, $R^3$, and $R^4$ are independently $C_1$-$C_{10}$ alkyl. More preferably, $R^1$, $R^2$, $R^3$, and $R^4$ are independently $C_1$-$C_6$ alkyl. Optionally, $R^1$ and $R^2$ or $R^3$ and $R^4$ may together form a ring.

Preferably, $R^1$ includes, but is not limited to, isobutyl, (2-hydroxy-2-methyl)propyl, hydroxymethyl, (3-amino)propyl, (4-amino)butyl, and the like. More preferably, $R^1$ is isobutyl.

Preferably, $R^3$ includes, but is not limited to, isobutyl, (tert-butyldimethylsilyloxy)methyl, (2-benzyloxy-2-methyl)propyl, 3-(benzylamino)propyl, 4-(benzylamino)butyl, and the like. More preferably, $R^3$ is isobutyl.

Preferably, $R^2$ and $R^4$ independently include, but are not limited to, hydrogen, ethoxymethyl, benzyl, (2-methoxy)ethyl, and the like. More preferably, $R^2$ and $R^4$ are hydrogen.

$R^3$ may be identical to or different from $R^1$. $R^4$ may be identical to or different from $R^2$. An example of when $R^3$ may be different from $R^1$ is when $R^1$ contains a nucleophilic moiety, such as an amino, hydroxyl, or thiol moiety. Preferably, when $R^1$ contains a nucleophilic moiety, $R^3$ is a suitably protected derivative of $R^1$. Preferably, when $R^2$ contains a nucleophilic moiety, $R^4$ is a suitably protected derivative of $R^2$.

A suitable protecting group is removable. If the protecting group is removed during the hydrolysis reaction, then $R^1$ (or $R^2$) will be different from $R^3$ (or $R^4$). A compilation of suitable protecting groups is found in Theodora W. Greene & Peter G. M. Wuts, Protective Groups in Organic Synthesis (3d ed. 1999). Examples of suitable protecting groups include, but are not limited to, benzyl and triphenylmethyl for an amino moiety, methoxymethyl and t-butyldimethylsilyl for a hydroxyl moiety, and p-methoxybenzyl and triphenylmethyl for a thiol moiety.

When $R^1$, $R^2$, $R^3$, and/or $R^4$ comprise an alkyl, cycloalkyl, alkenyl, cycloalkenyl, alkynyl, or aryl group that possesses a moiety, including a non-nucleophilic moiety, that is protected with a protecting group, the atoms of the protecting group do not affect the atom limitations expressed above. By way of example, the term "$C_1$-$C_6$ alkyl" includes, but is not limited to, 3-(t-butyloxycarbonylamino)propyl, because the t-butyloxycarbonyl (BOC) group is a protecting group. In other words, the 3-(BOC-amino)propyl group is a $C_3$ alkyl group possessing an amino moiety.

$R^5$, $R^6$, $R^7$, $R^8$, and $R^9$ are not critical. The $R^5$, $R^6$, $R^7$, $R^8$, and $R^9$ groups are part of an arylmethylamino side chain that is cleaved during the hydrolysis reaction. As such, the $R^5$, $R^6$, $R^7$, $R^8$, and $R^9$ groups are not present in the prepared acid addition salt of formula (5).

$R^5$, $R^6$, $R^7$, $R^8$, and $R^9$ may be identical or different. Preferably, each $R^5$, $R^6$, $R^7$, $R^8$, and $R^9$ for each of the n aryl rings independently includes, but is not limited to, hydrogen, $C_1$-$C_{10}$ alkyl, and $C_6$-$C_{20}$ aryl, $C_3$-$C_{10}$ cycloalkyl, $C_2$-$C_{10}$ alkenyl, $C_5$-$C_{10}$ cycloalkenyl, $C_6$-$C_{20}$ aryl, —$OR^{10}$, —$NR^{11}R^{12}$, and the like. Preferably, each $R^5$, $R^6$, $R^7$, $R^8$, and $R^9$ for each of the n aryl rings independently includes, but is not limited to, hydrogen, $C_1$-$C_{10}$ alkyl, $C_2$-$C_{10}$ alkenyl, $C_6$-$C_{20}$ aryl, —$OR^{10}$, —$NR^{11}R^{12}$, and the like. Preferably, each $R^5$, $R^6$, $R^7$, $R^8$, and $R^9$ for each of the n aryl rings independently includes, but is not limited to, hydrogen, $C_1$-$C_{10}$ alkyl, $C_6$-$C_{20}$ aryl, —$OR^{10}$, —$NR^{11}R^{12}$, and the like. Preferably, each $R^5$, $R^6$, $R^7$, $R^8$, and $R^9$ for each of the n aryl rings independently includes, but is not limited to, hydrogen, $C_1$-$C_{10}$ alkyl, —$OR^{10}$, and the like, wherein $R^{10}$ is $C_1$-$C_{10}$ alkyl. Preferably, each $R^5$, $R^6$, $R^7$, $R^8$, and $R^9$ for each of the n aryl rings independently includes, but is not limited to, hydrogen, $C_1$-$C_6$ alkyl, —$OR^{10}$, and the like, wherein $R^{10}$ is $C_1$-$C_6$ alkyl.

More preferably, each $R^5$, $R^6$, $R^7$, $R^8$, and $R^9$ for each of the n aryl rings is hydrogen. Optionally, R groups (i.e., $R^5$, $R^6$, $R^7$, $R^8$, and $R^9$) that are adjacent to one another may together form a ring (e.g., a phenyl ring).

Within $R^1$ to $R^9$, each alkyl, cycloalkyl, alkenyl, cycloalkenyl, alkynyl, and aryl group may contain up to four moieties, which include, but are not limited to, nitrogen-containing moieties (e.g., amino, amido, etc.), oxygen-containing moieties (e.g., hydroxyl, carboxyl, etc.), halogens, sulfur-containing moieties (e.g., thiol, sulfonyl, etc.), and the like.

Within $R^1$ to $R^9$, examples of $C_1$-$C_{10}$ alkyl groups include, but are not limited to, (tert-butyldimethylsilyloxy)methyl ($C_1$ having one oxygen-containing moiety—hydroxyl—protected by a tert-butyldimethylsilyl protecting group), isobutyl ($C_4$), ethoxymethyl ($C_3$ having one oxygen-containing moiety), (2-methoxy)ethyl ($C_3$ having one oxygen-containing moiety), and (2-benzyloxy-2-methyl)propyl ($C_4$ having one oxygen-containing moiety—hydroxyl—protected by a benzyl protecting group).

Within $R^1$ to $R^9$, examples of $C_2$-$C_{10}$ alkenyl groups include, but are not limited to, allyl ($C_3$), 2-methyl-2-butenyl ($C_5$), and 3-hexen-2-yl ($C_6$).

Within $R^1$ to $R^9$, examples of $C_2$-$C_{10}$ alkynyl groups include, but are not limited to, 2-butynyl ($C_4$), 4-phenyl-2-butynyl ($C_{10}$), and 4-methyl-2-pentynyl ($C_6$).

Within $R^1$ to $R^9$, examples of $C_3$-$C_{10}$ cycloalkyl groups include, but are not limited to, cyclopentyl ($C_5$), 2-(methyl)cyclohexyl ($C_7$), and 2-(N,N-(dibenzyl)amino)cyclohexyl ($C_6$ with a nitrogen-containing moiety—amino—protected by two benzyl protecting groups).

Within $R^1$ to $R^9$, examples of $C_5$-$C_{10}$ cycloalkenyl groups include, but are not limited to, cyclopentenyl ($C_5$), 4-(isopropyl)cyclohexenyl ($C_6$), and 4-(methyl)cyclohexenyl ($C_7$).

Within $R^1$ to $R^9$, examples of $C_6$-$C_{20}$ aryl groups include, but are not limited to, benzyl ($C_7$), tolyl ($C_7$), 2-(methyl)naphthyl ($C_{11}$), and 3-(cyano)isoquinolynyl ($C_{10}$ with two nitrogen-containing moieties (cyano and the ring nitrogen)).

The hydrolysis reaction may be performed at any suitable temperature. Preferably, the temperature is from room temperature (i.e., about 20° C.) to about 100° C.

The present hydrolysis method has unexpected advantages over the ammonolysis method of Scheme 1. The ammonolysis method requires heating at a high temperature (e.g., up to 155° C.) for a long time (e.g., up to 18 hours) in a sealed vessel. This sealed vessel reaction presents an undesirable safety risk. Surprisingly, the present hydrolysis method provides an acid addition salt of formula (5), and a 4-amino-1H-imidazo(4,5-c)quinoline therefrom, in high yield after a short reaction time without the use of a potentially dangerous sealed vessel reaction.

Furthermore, the present hydrolysis method has unexpected advantages over the hydrogenolysis method of Scheme 2. The hydrogenolysis reaction proceeds in low yield (e.g., 37%-42%) or not at all after a long reaction time (e.g., up to 2 days). Surprisingly, the present hydrolysis method provides acid addition salts of formula (5), and 4-amino-1H-imidazo(4,5-c)quinolines therefrom, in high yield after a short reaction time.

Ammonolysis, hydrogenolysis, and the present hydrolysis reactions represent distinct chemical reactions. These chemical reactions are used for different purposes, employ different reagents, and are conducted under different reaction conditions. Accordingly, these chemical reactions are not interchangeable. For example, an ammonolysis reaction cleaves a chemical bond with ammonia (i.e., $NH_3$), while a hydrogenolysis reaction cleaves a chemical bond with hydrogen (i.e., $H_2$). In contrast, a hydrolysis reaction cleaves a chemical bond with water (i.e., $H_2O$). Furthermore, while an ammonolysis reaction and a hydrogenolysis reaction often require the presence of a transition metal catalyst (e.g., copper, vanadium, titanium, palladium or ruthenium), the present hydrolysis reaction does not require a transition metal catalyst, and is instead performed in the presence of a strong acid catalyst. Finally, an ammonolysis reaction and a hydrogenolysis reaction often are performed in sealed vessels. In contrast, the present hydrolysis reaction is performed in open air.

One advantage of the present invention is that the hydrolysis reaction proceeds in high yield after a short reaction time. Preferably, the hydrolysis reaction provides the acid addition salt of formula (5) at a yield of at least about 50%. More preferably, the hydrolysis reaction provides the acid addition salt of formula (5) at a yield of at least about 60%. More preferably, the hydrolysis reaction provides the acid addition salt of formula (5) at a yield of at least about 70%. More preferably, the hydrolysis reaction provides the acid addition salt of formula (5) at a yield of at least about 80%.

Preferably, the hydrolysis reaction is conducted for a reaction time of less than about four hours. More preferably, the hydrolysis reaction is conducted for a reaction time of less than about three hours. More preferably, the hydrolysis reaction is conducted for a reaction time of less than about two hours. More preferably, the hydrolysis reaction is conducted for a reaction time of less than about one hour.

A further advantage of the present hydrolysis reaction is that it is generally applicable to many 4-(arylmethyl)amino-1H-imidazo(4,5-c)quinolines of formula (4). Without wishing to be bound by theory, it is believed that the compound of formula (4) may include many substituents at the $R^3$ and $R^4$ positions, as exemplified and disclosed herein, because these substituents are distant from the hydrolysis site (i.e., the C—N bond of the 4-(arylmethyl)amino group of the compound of formula (4)). It is further believed that the compound of formula (4) may include many substituents at the $R^5$ to $R^9$ positions, as exemplified and disclosed herein, because the strong acid used in the hydrolysis reaction is a powerful catalyst. It is further believed that in contrast to transition metal catalysts, the strong acid catalyst is much less susceptible to poisoning and deactivation by functional groups present in $R^3$ to $R^9$ (e.g., sulfur atoms). Accordingly, the strong acid is much more effective in catalyzing the hydrolysis of compounds of formula (4).

In accordance with the present invention, the 4-(arylmethyl)amino-1H-imidazo(4,5-c)quinoline of formula (4) may be prepared in any suitable manner. Suitable preparation methods include, but are not limited to, those disclosed in the '149 patent and the Shen article. Preferably, the 4-(arylmethyl)amino-1H-imidazo(4,5-c)quinoline of formula (4) is prepared by reacting an arylmethylamine of formula (3)

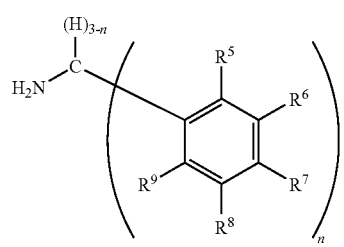

with a 4-chloro-1H-imidazo(4,5-c)quinoline of formula (2)

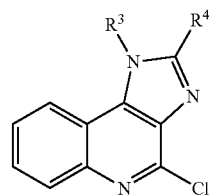

wherein n, $R^3$, $R^4$, $R^5$, $R^6$, $R^7$, $R^8$, and $R^9$ are defined as set forth above.

The arylmethylamine of formula (3) may be synthesized using methods well known to those of ordinary skill in the art. For example, benzaldehyde, benzophenone, or a suitable aryl ring-substituted derivative thereof, may be transformed into an arylmethylamine of formula (3) by reductive amination with ammonia and hydrogen ($H_2$) in the presence of a hydrogenation catalyst (see generally Jerry March, Advanced Organic Chemistry § 6-15 (3d ed. 1985)). In addition, many arylmethylamines of formula (3) are commercially available. For example, benzylamine, 2,4-dimethoxybenzylamine, diphenylmethylamine, and 1-(aminomethyl)naphthalene can be obtained from Sigma-Aldrich Corp. (St. Louis, Mo.). 1-(aminomethyl)naphthalene is an example of an arylmethylamine of formula (3), wherein adjacent R groups ($R^5$ and $R^6$) together form a ring (a phenyl ring).

Preferably, the arylmethylamine of formula (3) includes, but is not limited to, benzylamine, 2,4-dimethoxybenzylamine, diphenylmethylamine, 1-(aminomethyl)naphthalene, and the like.

The 4-chloro-1H-imidazo(4,5-c)quinoline of formula (2) may be synthesized according to known methods, such as the method disclosed in U.S. Pat. No. 4,689,338. 4-chloro-1-isobutyl-1H-imidazo(4,5-c)quinoline is commercially available from Auspure Biotechnology Co., Ltd. (Shanghai, China).

Any suitable temperature may be used to promote the addition/elimination reaction between the arylmethylamine of formula (3) and the 4-chloro-1H-imidazo(4,5-c)quinoline of formula (2). Preferably, the addition/elimination reaction is performed at a temperature of about 100° C. to about 140° C.

The arylmethylamine of formula (3) and the 4-chloro-1H-imidazo(4,5-c)quinoline of formula (2) may be present in the reaction mixture in any suitable amount. Preferably, an excess of the arylmethylamine of formula (3) is used. More preferably, the arylmethylamine of formula (3) and the 4-chloro-1H-imidazo(4,5-c)quinoline of formula (2) are present at a mole/mole ratio of at least about 2:1. More preferably, the arylmethylamine of formula (3) and the 4-chloro-1H-imidazo(4,5-c)quinoline of formula (2) are present at a mole/mole ratio of at least about 5:1.

The addition/elimination reaction between the arylmethylamine of formula (3) and the 4-chloro-1H-imidazo(4,5-c)quinoline of formula (2) may be performed either neat or in the presence of a suitable solvent. Suitable solvents include, but are not limited to, N,N-dimethylformamide (DMF), N,N-dimethylacetamide (DMA) and mixtures thereof. Preferably, the addition/elimination reaction is performed neat.

The present addition/elimination method has unexpected advantages over the addition/elimination method of Scheme 2. The addition/elimination method in Scheme 2 requires that the benzylamino intermediate is isolated by distilling away the reaction solvent, and optionally purified using silica gel column chromatography. These isolation and purification methods are costly and time consuming. Surprisingly, the present addition/elimination method provides a 4-(arylmethyl)amino-1H-imidazo(4,5-c)quinoline of formula (4) that does not require the product to be isolated or purified using these costly and inefficient procedures.

Preferably, the base is used in a quantity sufficient to raise the pH of the reaction mixture to at least about 8. More preferably, the base is used in a quantity sufficient to raise the pH of the reaction mixture to at least about 10.

Any suitable method may be used to isolate the 4-amino-1H-imidazo(4,5-c)quinoline of formula (1). Suitable isolation methods include, but are not limited to, filtration and extraction.

Any suitable method may be used to purify the 4-amino-1H-imidazo(4,5-c)quinoline of formula (1). Suitable purification methods include, but are not limited to, slurrying, crystallizing, and chromatography. Suitable slurrying and crystallizing solvents include, but are not limited to, DMF. Additional methods of isolation and purification are well known to those of ordinary skill in the art.

In accordance with the present invention, two additional embodiments are provided, which involve modified hydrogenolysis methods for the preparation of 4-amino-1H-imidazo(4,5-c)quinolines (Scheme 3).

Scheme 3

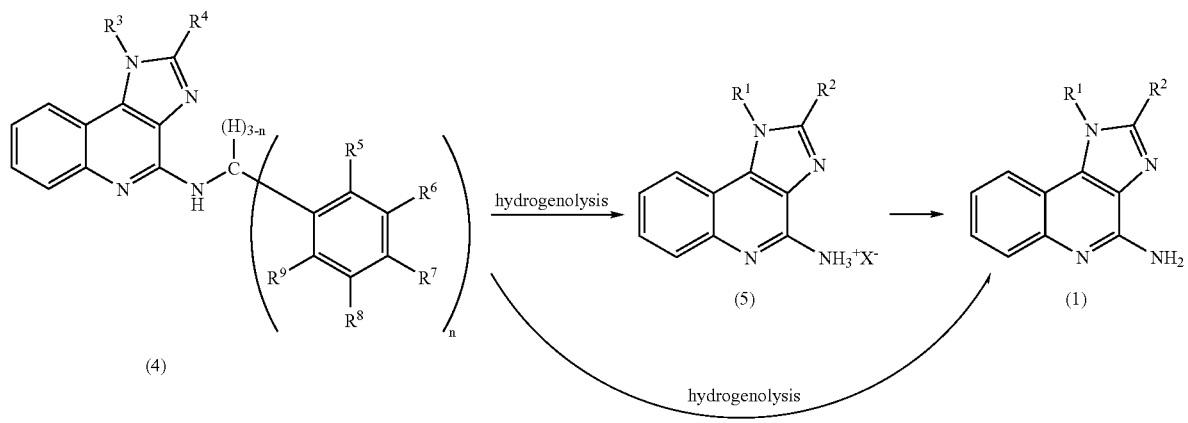

A further advantage of the present invention is that the addition/elimination reaction between the arylmethylamine of formula (3) and the 4-chloro-1H-imidazo(4,5-c)quinoline of formula (2) may be performed without a sealed reaction vessel at atmospheric pressure. Another further advantage of the present invention is that the addition/elimination reaction proceeds in high yield after a short reaction time.

In accordance with the present invention, the method further comprises the step of treating the acid addition salt of formula (5) with a base to provide a 4-amino-1H-imidazo(4,5-c)quinoline of formula (1)

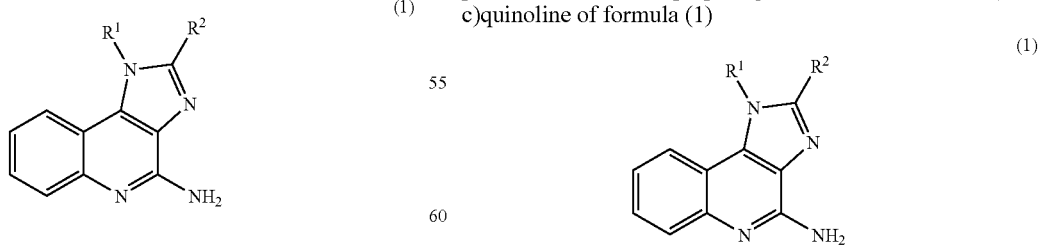

wherein $R^1$ and $R^2$ are defined as set forth above.

The acid addition salt of formula (5) may be treated with any suitable base. Preferably, an aqueous base is used. More preferably, the base is sodium hydroxide, potassium hydroxide or a mixture thereof. More preferably, the base is sodium hydroxide.

The first modified hydrogenolysis method (i.e., the first additional embodiment) involves transforming a 4-(arylmethyl)amino-1H-imidazo(4,5-c)quinoline of formula (4) into a 4-amino-1H-imidazo(4,5-c)quinoline of formula (1). The second modified hydrogenolysis method (i.e., the second additional embodiment) involves transforming a 4-(arylmethyl)amino-1H-imidazo(4,5-c)quinoline of formula (4) into an acid addition salt of formula (5), which in turn is converted into a 4-amino-1H-imidazo(4,5-c)quinoline of formula (1).

In the first additional embodiment, the present invention provides a method of preparing a 4-amino-1H-imidazo(4,5-c)quinoline of formula (1)

(1)

comprising the step of hydrogenolyzing a 4-(arylmethyl)amino-1H-imidazo(4,5-c)quinoline of formula (4) with Pearlman's catalyst and hydrogen ($H_2$) in the absence of an acid

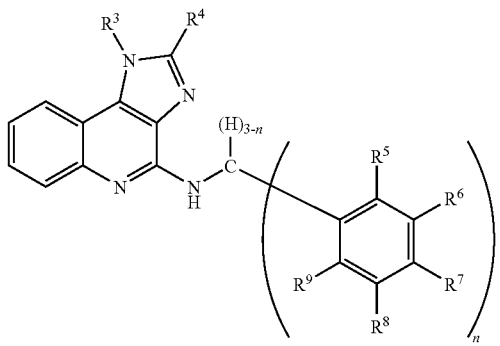

(4)

wherein n, $R^1$, $R^2$, $R^3$, $R^4$, $R^5$, $R^6$, $R^7$, $R^8$, and $R^9$ are defined as set forth above.

Pearlman's catalyst ($Pd(OH)_2$ on carbon) is commercially available from Sigma-Aldrich Corp. (St. Louis, Mo.). Preferably, the hydrogenolysis reaction is performed in the presence of a second catalyst in addition to Pearlman's catalyst. Suitable second catalysts include, but are not limited to, triethylamine.

The hydrogenolysis reaction may be performed at any suitable pressure. Preferably, the hydrogenolysis reaction is performed at a hydrogen ($H_2$) pressure of about 1 atmosphere.

Any suitable solvent may be used for hydrogenolysis reaction. Suitable solvents include, but are not limited to, alcoholic solvents and ethyl acetate.

Preferably, the 4-(arylmethyl)amino-1H-imidazo(4,5-c) quinoline of formula (4) is prepared by the addition/elimination reaction of an arylmethylamine of formula (3) with a 4-chloro-1H-imidazo(4,5-c)quinoline of formula (2), as set forth above.

The 4-amino-1H-imidazo(4,5-c)quinoline of formula (1) prepared in the hydrogenolysis reaction may be isolated using any suitable method. Suitable isolation methods include, but are not limited to, adding water to the reaction mixture, and filtering or decanting. The isolated 4-amino-1H-imidazo(4,5-c)quinoline of formula (1) may be purified as set forth above.

In the second additional embodiment, the present invention provides a method of preparing an acid addition salt of formula (5)

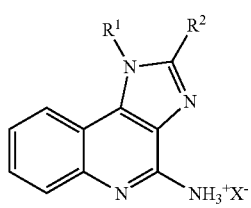

(5)

comprising the step of hydrogenolyzing a 4-(arylmethyl) amino-1H-imidazo(4,5-c)quinoline of formula (4) with Pearlman's catalyst and hydrogen ($H_2$) in the presence of an acid, HX

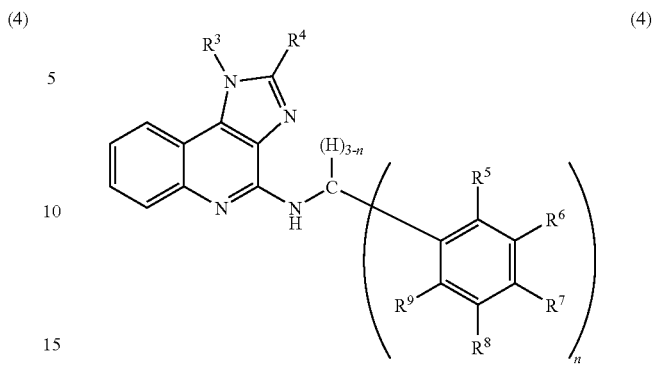

(4)

wherein n, $R^1$, $R^2$, $R^3$, $R^4$, $R^5$, $R^6$, $R^7$, $R^8$, and $R^9$ are defined as set forth above.

Suitable acids, HX, for use in the hydrogenolysis reaction include, but are not limited to, formic acid, acetic acid, and trifluoroacetic acid. The conjugate bases, $X^-$, of those acids are $HCOO^-$, $CH_3COO^-$, and $CF_3COO^-$, respectively. Formic acid may function as an internal source of hydrogen ($H_2$). Consequently, when formic acid is used, an external source of hydrogen ($H_2$) is not necessary. Preferably, the hydrogenolysis reaction is conducted in a hydrogen ($H_2$) atmosphere.

Preferably, the hydrogenolysis reaction is performed using at least about one molar equivalent of an acid, HX, based on the molar quantity of the 4-(arylmethyl)amino-1H-imidazo (4,5-c)quinoline of formula (4) present in the reaction. More preferably, when the acid is formic acid, a large molar excess of formic acid is used. More preferably, the hydrogenolysis reaction is performed using formic acid as the solvent.

The hydrogenolysis reaction may be performed at a hydrogen ($H_2$) pressure of greater than 1 atmosphere. Preferably, the hydrogenolysis reaction is performed at a hydrogen pressure of about 1 atmosphere.

Suitable solvents for the hydrogenolysis reaction include, but are not limited to, alcoholic solvents and ethyl acetate.

Preferably, the 4-(arylmethyl)amino-1H-imidazo(4,5-c) quinoline of formula (4) is prepared by the addition/elimination reaction of an arylmethylamine of formula (3) with a 4-chloro-1H-imidazo(4,5-c)quinoline of formula (2), as set forth above.

The acid addition salt of formula (5) prepared in the hydrogenolysis reaction may be treated with any suitable base to provide a 4-amino-1H-imidazo(4,5-c)quinoline of formula (1), as set forth above.

The prepared 4-amino-1H-imidazo(4,5-c)quinoline of formula (1) may be isolated and purified as set forth above.

Accordingly, the present invention provides a method of preparing 4-amino-1H-imidazo(4,5-c)quinolines of formula (1) and acid addition salts of formula (5) in high yield and purity from the corresponding 4-(arylmethyl)amino-1H-imidazo(4,5-c)quinolines of formula (4). The present method is safe, simple, rapid, economical, and suitable for industrial preparations. The present invention is illustrated, but not limited by the following examples.

EXAMPLES

Example 1

Synthesis of
4-amino-1-isobutyl-1H-imidazo(4,5-c)quinoline
(Imiquimod)

In this study, imiquimod was prepared in three steps, starting from 4-chloro-1-isobutyl-1H-imidazo(4,5-c)quinoline (compound of formula (2)).

Step 1: Preparation of 4-(N-benzylamino)-1-isobutyl-1H-imidazo(4,5-c)quinoline (Compound of Formula (4))

In a three-necked 100-mL flask, equipped with a thermometer, 20 grams of benzylamine and 10 grams of 4-chloro-1-isobutyl-1H-imidazo(4,5-c)quinoline were added with stirring. The resulting slurry was heated to 120° C.-130° C., and the reaction monitored by Thin Layer Chromatography (TLC; RP-18; mobile phase=80% acetonitrile:20% water).

When the TLC indicated the disappearance of 4-chloro-1-isobutyl-1H-imidazo(4,5-c)quinoline, the reaction mixture was cooled to room temperature resulting in a solid mass. 60 mL of water was added and the reaction mixture was stirred for 30 min. The solids were then separated by filtration and the solids were washed with 20 mL of water. The solids were then dried in an oven at 85° C. resulting in 11.3 grams (90% yield) of 4-(N-benzylamino)-1-isobutyl-1H-imidazo(4,5-c)quinoline.

Step 2: Preparation of Acid Addition Salt (Compound of Formula (5))

1 gram of 4-(N-benzylamino)-1-isobutyl-1H-imidazo(4,5-c)quinoline was added to 5 mL of aqueous 96%-98% sulfuric acid with stirring in a 100-mL flask at 22° C.-25° C. After about 5-10 minutes the reaction mixture became clear. After about 30 minutes, TLC (normal phase, mobile phase=5% methanol: 95% chloroform) indicated the reaction was complete, and 10 mL water was slowly added.

Step 3: Preparation of 4-amino-1-isobutyl-1H-imidazo(4,5-c)quinoline (Compound of Formula (1))

The flask was cooled in an ice bath, and an aqueous solution of about 10% sodium hydroxide was slowly added to the mixture from step (b) until a pH of about 12 was achieved. The suspension was stirred for 15 minutes. The mixture was filtered, and the collected solids were washed with water. The solid was dried at 85° C., providing 0.63 gram of 4-amino-1-isobutyl-1H-imidazo(4,5-c)quinoline (85% yield from 4-(N-benzylamino)-1-isobutyl-1H-imidazo(4,5-c)quinoline).

Example 2

Synthesis of
4-amino-1-isobutyl-1H-imidazo(4,5-c)quinoline
(Imiquimod)

In this study, imiquimod was prepared using the general three-step method exemplified in Example 1. However, different concentrations of sulfuric acid and sodium hydroxide were used in the second and third steps, respectively.

Step 1: Preparation of 4-(N-benylamino)-1-isobutyl-1H-imidazo(4,5-c)quinoline (Compound of Formula (4))

4-(N-benzylamino)-1-isobutyl-1H-imidazo(4,5-c)quinoline was prepared using the general method exemplified in Example 1.

Step 2: Preparation of Acid Addition Salt (Compound of Formula (5))

In a three-necked 500-mL flask, equipped with mechanical stirrer and thermometer, 60 mL of aqueous 30%-70% sulfuric acid was introduced. 20 grams of 4-(N-benzylamino)-1-isobutyl-1H-imidazo(4,5-c)quinoline were added, causing the temperature to increase to 75° C. The mixture was heated between 70° C. and 100° C. until TLC indicated the reaction was complete (about 1 hour).

The reaction mixture was cooled to 70° C., and 60 mL of toluene was added. Then, 240 mL of water was added dropwise, keeping the temperature less than 60° C. When all the water was added, the reaction was cooled to about room temperature, then to 10° C., and then stirred at 10° C. for 30 minutes. The acid addition salt (compound of formula (5)) was filtered and the cake was washed with water.

Step 3: Preparation of 4-amino-1-isobutyl-1H-imidazo(4,5-c)quinoline (Compound of Formula (1))

The acid addition salt (compound of formula (5)) was slurried in 30 mL of water at room temperature for 15 minutes, and then 20 mL of an aqueous solution of 20% NaOH was added. The slurry was stirred for 1 hour, while ensuring that the pH was at least about 8. The mixture was filtered, and the collected solids were washed with water. The solid was dried, providing 11.9 grams of 4-amino-1-isobutyl-1H-imidazo(4,5-c)quinoline (82% yield from 4-(N-benzylamino)-1-isobutyl-1H-imidazo(4,5-c)quinoline).

Example 3

Synthesis of
4-amino-1-isobutyl-1H-imidazo(4,5-c)quinoline
(Imiquimod)

In this study, imiquimod was prepared using the general three-step method exemplified in Examples 1 and 2. However, a different procedure was used to isolate the acid addition salt.

Step 1: Preparation of 4-(N-benzylamino)-1-isobutyl-1H-imidazo(4,5-c)quinoline (Compound of Formula (4))

4-(N-benzylamino)-1-isobutyl-1H-imidazo(4,5-c)quinoline was prepared using the general method exemplified in Example 1.

Step 2: Preparation of Acid Addition Salt (Compound of Formula (5)

In a three-necked 500-mL flask, equipped with mechanical stirrer and thermometer, 60 mL of aqueous 70% $H_2SO_4$ was introduced. 20 grams of 4-(N-benzylamino)-1-isobutyl-1H-imidazo(4,5-c)quinoline was added, causing the temperature to increase to about 75° C. The mixture was heated to about 100° C. until TLC indicated the reaction was complete (about 1 hour). The reaction mixture was cooled to about 80° C., 80 mL of toluene was added, and the mixture was stirred for 15 min. 180 mL of 10% HCl was then added, which caused the temperature to increase to about 85° C.-90° C. The resulting clear mixture was cooled to 70° C. and hot filtered. The two layers of the filtrate were separated, and the upper organic layer discarded. 180 mL of water was added to the acidic aqueous layer, and the mixture was cooled to room temperature. The hydrochloride salt precipitated and was isolated by filtration and washed with water.

Step 3: Preparation of 4-amino-1-isobutyl-1H-imidazo(4,5-c)quinoline (Compound of Formula (1))

The isolated acid addition salt was suspended in ~22% NaOH solution (100 mL) at room temperature for 30 minutes. The mixture was filtered and the collected solids were washed with water and dried, providing 10.9 grams of 4-amino-1-isobutyl-1H-imidazo(4,5-c)quinoline (85% yield from 4-(N-benzylamino)-1-isobutyl-1H-imidazo(4,5-c)quinoline).

Example 4

Synthesis of 4-amino-1-isobutyl-1H-imidazo(4,5-c)quinoline (Imiquimod)

In this study, imiquimod is prepared in three steps, starting from 4-chloro-1-isobutyl-1H-imidazo(4,5-c)quinoline (compound of formula (2)). However, the intermediate acid addition salt is prepared using Pearlman's catalyst and hydrogen.

Step 1: Preparation of 4-(N-benzylamino)-1-isobutyl-1H-imidazo(4,5-c)quinoline (Compound of Formula (4))

4-(N-benzylamino)-1-isobutyl-1H-imidazo(4,5-c)quinoline is prepared using the general method exemplified in Example 1.

Step 2: Preparation of Acid Addition Salt (Compound of Formula (5))

1.0 gram of 4-(N-benzylamino)-1-isobutyl-1H-imidazo(4,5-c)quinoline is added to 10 mL of isopropyl alcohol followed by the addition of 1.1 equiv. of trifluoroacetic acid and 0.2 gram of Pearlman's catalyst (20% Pd(OH)$_2$/C). The mixture is stirred at 50° C. under 1 atm hydrogen until completion. The mixture is filtered through Celite® (available from Sigma-Aldrich Corp. (St. Louis, Mo.)) and the filtrate, containing acid addition salt (compound of formula (5)), is concentrated in vacuo.

Step 3: Preparation of 4-amino-1-isobutyl-1H-imidazo(4,5-c)quinoline (Compound of Formula (1))

Acid addition salt (compound of formula (5)) is suspended in 10 mL of water followed by the slow addition of 10% sodium hydroxide until a pH of about 12 is achieved. The suspension is filtered, and the collected solids are washed with water and dried, providing 4-amino-1-isobutyl-1H-imidazo(4,5-c)quinoline (imiquimod).

Example 5

Synthesis of 4-amino-1-isobutyl-1H-imidazo(4,5-c)quinoline (Imiquimod)

In this study, imiquimod is prepared using the general three-step method exemplified in Example 4. However, the acid addition salt is prepared using Pearlman's catalyst without hydrogen.

Step 1: Preparation of 4-(N-benzylamino)-1-isobutyl-1H-imidazo(4,5-c)quinoline (Compound of Formula (4))

4-(N-benzylamino)-1-isobutyl-1H-imidazo(4,5-c)quinoline is prepared using the general method exemplified in Example 1.

Step 2: Preparation of Acid Addition Salt (Compound of Formula (5))

1.0 gram of 4-(N-benzylamino)-1-isobutyl-1H-imidazo(4,5-c)quinoline is added to 20 mL formic acid. 0.2 gram of Pearlman's catalyst (20% Pd(OH)$_2$/C) is added. The mixture is heated at reflux until completion. The mixture is filtered through Celite® and the filtrate, containing acid addition salt (compound of formula (5)), is concentrated in vacuo.

Step 3: Preparation of 4-amino-1-isobutyl-1H-imidazo(4,5-c)quinoline (Compound of Formula (1))

4-amino-1-isobutyl-1H-imidazo(4,5-c)quinoline (compound of formula (1)) is prepared using the general method exemplified in Example 4.

Example 6

Synthesis of 4-amino-1-isobutyl-1H-imidazo(4,5-c)quinoline (Imiquimod)

In this study, imiquimod is prepared using the general three-step method exemplified in Examples 4 and 5. However, the acid addition salt is prepared using Pearlman's catalyst, formic acid, and hydrogen.

Step 1: Preparation of 4-(N-benzylamino)-1-isobutyl-1H-imidazo(4,5-c)quinoline (Compound of Formula (4))

4-(N-benzylamino)-1-isobutyl-1H-imidazo(4,5-c)quinoline is prepared using the general method exemplified in Example 1.

Step 2: Preparation of Acid Addition Salt (Compound of Formula (5))

1.0 gram of 4-(N-benzylamino)-1-isobutyl-1H-imidazo(4,5-c)quinoline is added to 20 mL formic acid. 0.2 gram of Pearlman's catalyst (20% Pd(OH)$_2$/C) is added. The mixture is stirred at 50° C. under 1 atm hydrogen until completion. The mixture is filtered through Celite® and the filtrate, containing acid addition salt (compound of formula (5)), is concentrated in vacuo.

Step 3: Preparation of 4-amino-1-isobutyl-1H-imidazo(4,5-c)quinoline (Compound of Formula (1))

4-amino-1-isobutyl-1H-imidazo(4,5-c)quinoline (compound of formula (1)) is prepared using the general method exemplified in Example 4.

Example 7

Synthesis of 4-amino-1-isobutyl-1H-imidazo(4,5-c)quinoline (Imiquimod)

In this study, imiquimod is prepared in two steps starting from 4-chloro-1-isobutyl-1H-imidazo(4,5-c)quinoline (compound of formula (2)). The second step is performed using Pearlman's catalyst and triethylamine as an additional catalyst.

Step 1: Preparation of 4-(N-benzylamino)-1-isobutyl-1H-imidazo(4,5-c)quinoline (Compound of Formula (4))

4-(N-benzylamino)-1-isobutyl-1H-imidazo(4,5-c)quinoline is prepared using the general method exemplified in Example 1.

Step 2: Preparation of 4-amino-1-isobutyl-1H-imidazo(4,5-c)quinoline 1.0 gram of 4-(N-benzylamino)-1-isobutyl-1H-imidazo(4,5-c)quinoline is added to 10 mL of ethanol, followed by the addition of 0.03 gram triethylamine and 0.2 gram of Pearlman's catalyst (20% Pd(OH)$_2$/C). The mixture is stirred at 40° C. under 1 atm hydrogen until completion. The mixture is then filtered through Celite® and the filtrate, containing 4-amino-1-isobutyl-1H-imidazo(4,5-c)quinoline (imiquimod), is concentrated in vacuo.

The citation and discussion of references in this specification is provided merely to clarify the description of the present invention and is not an admission that any such reference is "prior art" to the invention described herein. All references cited and discussed in this specification are incorporated herein by reference in their entirety.

What is claimed is:
1. A method of preparing an acid addition salt of formula (5)

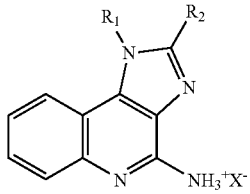

consisting of the step of hydrolyzing a 4-(arylmethyl)amino-1H-imidazo(4,5-c)quinoline of formula (4) with a strong acid, HX,

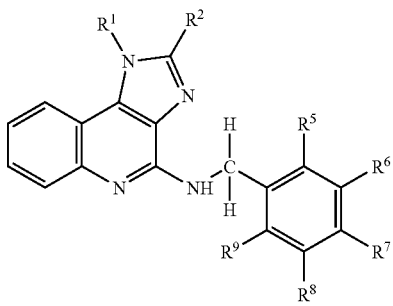

wherein
R$^1$ and R$^2$ are independently selected from the group consisting of hydrogen, C$_1$-C$_4$ alkyl, C$_3$-C$_4$ cycloalkyl, C$_2$-C$_4$ alkenyl, and C$_2$-C$_4$ alkynyl,
each of R$^5$, R$^6$, R$^7$, R$^8$, and R$^9$ is hydrogen, and
X$^-$ is a conjugate base of a strong acid,
thereby forming an acid addition salt of formula (5), wherein at least one of R$^1$ and R$^2$ is hydrogen.

2. The method of claim 1, wherein the 4-(arylmethyl)amino-1H-imidazo(4,5-c)quinoline of formula (4) is prepared by reacting benzylamine with a 4-chloro-1H-imidazo(4,5-c)quinoline of formula (2)

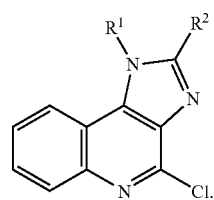

3. The method of claim 1, wherein the strong acid is selected from the group consisting of sulfuric acid, methanesulfonic acid, trifluoromethanesulfonic acid, and mixtures thereof.

4. The method of claim 1, further comprising treating the acid addition salt of formula (5) with a base to provide a 4-amino-1H-imidazo(4,5-c)quinoline of formula (1)

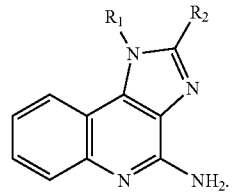

5. The method of claim 4, wherein the base is selected from the group consisting of sodium hydroxide, potassium hydroxide, and mixtures thereof.

6. The method of claim 4, wherein the 4-amino-1H-imidazo(4,5-c)quinoline of formula (1) is 4-amino-1-isobutyl-1H-imidazo[4,5-c]quinoline.

7. The method of claim 1, wherein the hydrolyzing step is performed for less than about four hours.

8. The method of claim 1, wherein the hydrolyzing step is performed for less than about two hours.

9. The method of claim 1, wherein the hydrolyzing step provides the acid addition salt of formula (5) at a yield of at least about 70%.

10. The method of claim 1, wherein the hydrolyzing step provides the acid addition salt of formula (5) at a yield of at least about 80%.

11. The method of claim 2, wherein the 4-(arylmethyl) amino-1H-imidazo(4,5-c)quinoline of formula (4) is prepared in a neat reaction.

12. The method of claim 2, wherein the 4-(arylmethyl) amino-1H-imidazo(4,5-c)quinoline of formula (4) is prepared at a temperature of about 100° C. to about 140° C.

13. The method of claim 1, wherein $R^1$ and $R^2$ are independently selected from the group consisting of hydrogen and $C_1$-$C_4$ alkyl.

14. The method of claim 13, wherein the 4-(arylmethyl) amino-1H-imidazo(4,5-c)quinoline of formula (4) is prepared by reacting benzylamine with a 4-chloro-1H-imidazo (4,5-c)quinoline of formula (2)

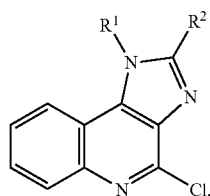

(2)

15. The method of claim 1, comprising preparing an acid addition salt of formula (25)

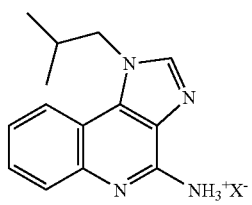

(25)

consisting of hydrolyzing 4-(N-benzylamino)-1-isobutyl-1H-imidazo(4,5-c)quinoline (formula (24)) with the strong acid, HX,

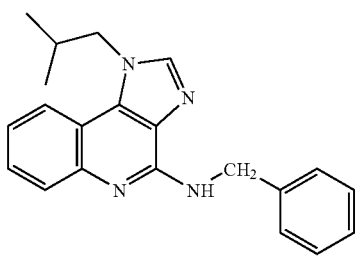

(24)

thereby forming the acid addition salt of formula (25).

16. The method of claim 15, wherein the 4-(N-benzylamino)-1-isobutyl-1H-imidazo(4,5-c)quinoline (formula (24)) is prepared by reacting benzylamine with 4-chloro-1-isobutyl-1H-imidazo(4,5-c)quinoline (formula (22))

(22)

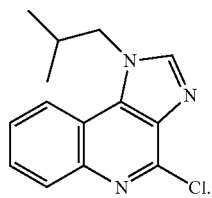

17. The method of claim 1, wherein $R^1$ is hydrogen and $R^2$ is isobutyl.

18. The method of claim 17, wherein the 4-(arylmethyl) amino-1H-imidazo(4,5-c)quinoline of formula (4) is prepared by reacting benzylamine with a 4-chloro-1H-imidazo (4,5-c)quinoline of formula (2)

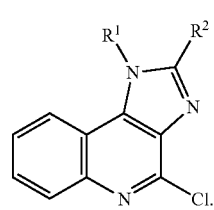

(2)

19. The method of claim 1, wherein the strong acid is sulfuric acid.

20. A method of preparing an acid addition salt of formula (5)

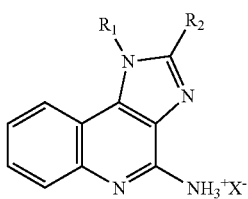

(5)

consisting essentially of the step of hydrolyzing a 4-(arylmethyl)amino-1H-imidazo(4,5-c)quinoline of formula (4) with a strong acid, HX,

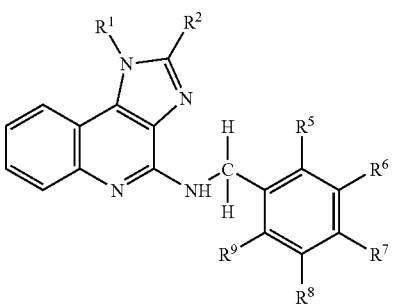

(4)

wherein
$R^1$ and $R^2$ are independently selected from the group consisting of hydrogen, $C_1$-$C_4$ alkyl, $C_3$-$C_4$ cycloalkyl, $C_2$-$C_4$ alkenyl, and $C_2$-$C_4$ alkynyl,
each of $R^5$, $R^6$, $R^7$, $R^8$, and $R^9$ is hydrogen, and
$X^-$ is a conjugate base of a strong acid,
thereby forming an acid addition salt of formula (5), wherein at least one of R1 and R2 is hydrogen.

* * * * *